United States Patent
Nelson

(10) Patent No.: US 9,330,240 B2
(45) Date of Patent: May 3, 2016

(54) METHOD AND SYSTEM OF IDENTIFYING BODILY IMBALANCES

(71) Applicant: Bradley Nelson, St. George, UT (US)

(72) Inventor: Bradley Nelson, St. George, UT (US)

( * ) Notice: Subject to any disclaimer, the term of this patent is extended or adjusted under 35 U.S.C. 154(b) by 159 days.

(21) Appl. No.: 14/021,601

(22) Filed: Sep. 9, 2013

(65) Prior Publication Data
US 2015/0073307 A1 Mar. 12, 2015

(51) Int. Cl.
A61B 5/00 (2006.01)
G06F 19/00 (2011.01)
A61B 5/11 (2006.01)

(52) U.S. Cl.
CPC .............. *G06F 19/363* (2013.01); *A61B 5/1101* (2013.01); *A61B 5/4023* (2013.01); *A61B 5/4076* (2013.01)

(58) Field of Classification Search
CPC ...... A61B 5/40; A61B 5/4023; A61B 5/4076; A61B 5/41; A61B 5/11; A61B 5/1101; A61B 5/1124; A61B 5/1125; G06F 19/363
See application file for complete search history.

(56) References Cited

U.S. PATENT DOCUMENTS

| 5,855,539 A | 1/1999 | Wise |
| 7,871,377 B2 | 1/2011 | Vainshelboim et al. |
| 8,323,216 B2 | 12/2012 | Fabian |
| 8,740,794 B2 * | 6/2014 | Scott ..................... A61B 5/1124 600/301 |
| 8,934,954 B2 * | 1/2015 | Brunswick ........... A61B 5/0531 600/346 |
| 2005/0056290 A1 | 3/2005 | Feinberg |
| 2013/0172693 A1 | 7/2013 | Lubelchick |

* cited by examiner

*Primary Examiner* — Max Hindenburg
(74) *Attorney, Agent, or Firm* — Gurr & Brande, PLLC; Robert A. Gurr

(57) ABSTRACT

In one embodiment, a method of identifying bodily imbalances comprises presenting a mind map to a subject; asking the subject a question based on the mind map; performing muscle response testing; and, identifying the imbalance. The mind map may be presented in printed form, using an electronic means, or presented verbally. The mind map further comprises six (6) categories: pathogenic imbalances, structural imbalances, nutritional imbalances, circuitry imbalances, toxic imbalances, and energetic imbalances; and a series of subcategories within each category.

16 Claims, 4 Drawing Sheets

METHOD AND SYSTEM OF IDENTIFYING BODILY IMBALANCES

TECHNICAL FIELD

The present technology relates to bodily health and function. More particularly, the present technology relates to using muscle response testing and a series of steps (a "mind map") to aid in identifying bodily imbalances.

BACKGROUND

Various methods exist, both in standard and alternative medicines, for diagnosing a patient. Perhaps the easiest method of diagnosis is by physical examination. For example, a compound fracture is easily seen by the naked eye, and no further analysis may be required (ignoring other potential internal injuries to the area of the fracture). However, if the malady is unseen to the naked eye, the patient is usually questioned to further determine the problem. For example, when someone complains of abdominal pains, the physician may inquire where, in particular, the pain exists (e.g., to rule out appendicitis or other possibilities) or may inquire what the person has recently eaten or the activities they have been involved in. If the physician is still unable to determine the problem, more invasive procedures are usually recommended, such as obtaining bodily fluids, performing scans, and in some instances, even exploratory surgery. However, before invasive procedures are used, many physicians take alternative approaches, such as chiropractic, massage, laser, essential oils, herbs and other supplements, and the like. However, often times the treatment may not work correctly or may be prolonged due to the treating physician not knowing the underlying cause of the problem. In an effort to overcome this problem, many alternative physicians have turned to the unconscious mind. It is estimated that the unconscious mind comprises around 90-96% of human intelligence. As such, physicians began to look to ways of using such a great resource.

Muscle response testing is a form of biofeedback that allows the treating physician to get responses from the subconscious mind of a patient. The treating physician usually asks the patient questions, then tests the patient's muscles for either a "yes" or "no" response, indicated, respectively, by either relative strength or weakness of the indicator muscle. However, these "yes" and "no" answers may not lead to a proper identification if the treating physician does not ask the appropriate question, or is unfamiliar with the problem encountered. As such, there is a need in the industry for a system that guides a treating physician when using muscle response testing to identify bodily imbalances. The current method and system seek to solve this and other problems.

SUMMARY OF EXAMPLE EMBODIMENTS

In one embodiment, a method of identifying bodily imbalances comprises presenting a mind map to a subject; asking the subject a question based on the mind map; performing muscle response testing; and, identifying the imbalance. The mind map may be presented in printed form, using an electronic means, or presented verbally. The mind map further comprises six (6) categories: pathogenic imbalances, structural imbalances, nutritional imbalances, circuitry imbalances, toxic imbalances, and energetic imbalances; and a series of subcategories within each category.

In one embodiment, the mind map comprises a book or binder with a series of tabs directing a user from one section and/or to another, and then further within each section, until an identification is reached.

In an embodiment, the mind map comprises an electronic means for interacting with a series of links until a final identification is made. In one embodiment the electronic means comprises a computer readable medium, such as a compact disc, ROM memory, or flash memory, that is inserted or otherwise installed onto a personal computer or other computing device. In another embodiment, the electronic means comprises hosting the media on a $3^{rd}$ party location, such as a server, wherein a user may connect to the server using a capable device (e.g. a personal computer directly connected to the server, over the internet, or use of virtual servers) and interact with the links. In yet another embodiment, the electronic means comprises hosting a website wherein a user may access the links from any internet-capable device, such as a personal computer, tablet, smartphone, or other device. The website hosting being accomplished according to the standards and methods known to those in the art.

DETAILED DESCRIPTION OF EXAMPLE EMBODIMENTS

The following descriptions depict only example embodiments and are not to be considered limiting of its scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention. Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various different sequences and arrangements while still falling within the scope of the present invention.

As used herein, the term "user" may be a physician, a subject or patient, or other person that is using the present technology to identify an imbalance for themselves or others. The term "subject" is defined as the affected person seeking an identification of a bodily imbalance.

Figure 4:
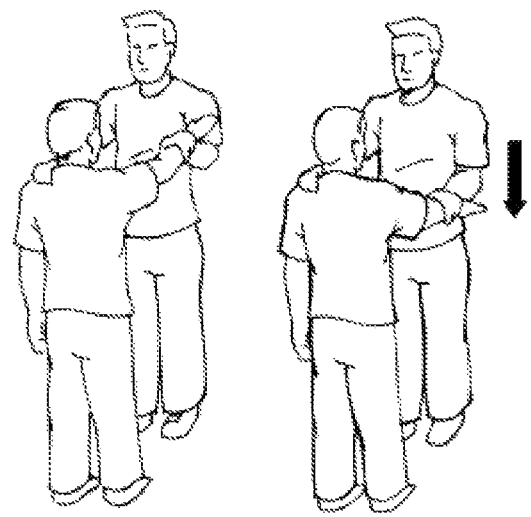
FIG. 4 illustrates a tester performing muscle response testing on a subject using the subject's full arm.
Figure 5:
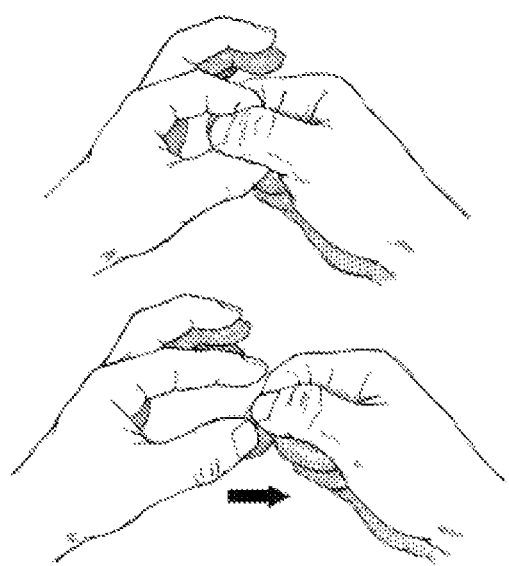
FIG. 5 illustrates a method of performing muscle response testing using thumbs and fingers.

In one embodiment, a method of identifying bodily imbalances comprises presenting a mind map to a subject; asking the subject a question based on the mind map; performing muscle response testing; and, identifying the imbalance. The mind map may be presented in printed form, using an electronic means, or presented verbally. Muscle response testing is well known in the medical industry, and is particularly used by alternative physicians (e.g., chiropractors, holistic physicians, etc.). The physician or person doing the testing (the "tester," but may also be a "user" if identifying an imbalance in oneself) typically asks the subject a "yes" or "no" question and then applies some physical pressure to the subject (e.g., as generally shown in FIG. 4, pushing an arm down from a horizontal position or, as shown generally in FIG. 5, pulling a finger through a loop made by the thumb and index finger) in order to ascertain an answer from the subject's subconscious portion of the mind. However, multiple methods exist for testing a subject, and often the tester does not know the proper questions to ask. Therefore, in one embodiment, a mind map (see generally FIG. 1) is used when the tester is performing muscle response testing. The mind map comprises six (6) categories: pathogenic imbalances, structural imbalances, nutritional imbalances, circuitry imbalances, toxic imbalances, and energetic imbalances. It will be appreciated that while the categories have been given specific names herein, equivalent categories, regardless of nomenclature, are likewise contemplated herein. In other words, the categories are more particularly defined as follows:

1. Pathogenic imbalance: Micro or macro organisms that inhabit the body such as viral, bacterial, fungal or parasitic infections.
2. Structural imbalance: Misalignment or subluxation of bone, organ, muscle, nerve, tendon or other tissue, resulting in impaired function.
3. Nutritional imbalance: Improper pH, deficiency of vitamins, minerals, etc.
4. Circuitry imbalance: Imbalance of organs, glands, chakras and acupuncture meridians, etc.
5. Toxic imbalance: The presence of heavy metals, free radicals, chemical toxins, etc.
6. Energetic imbalance: The presence of "trapped" emotional energies, the energy from physical trauma to the body, etc.

Figure 1:
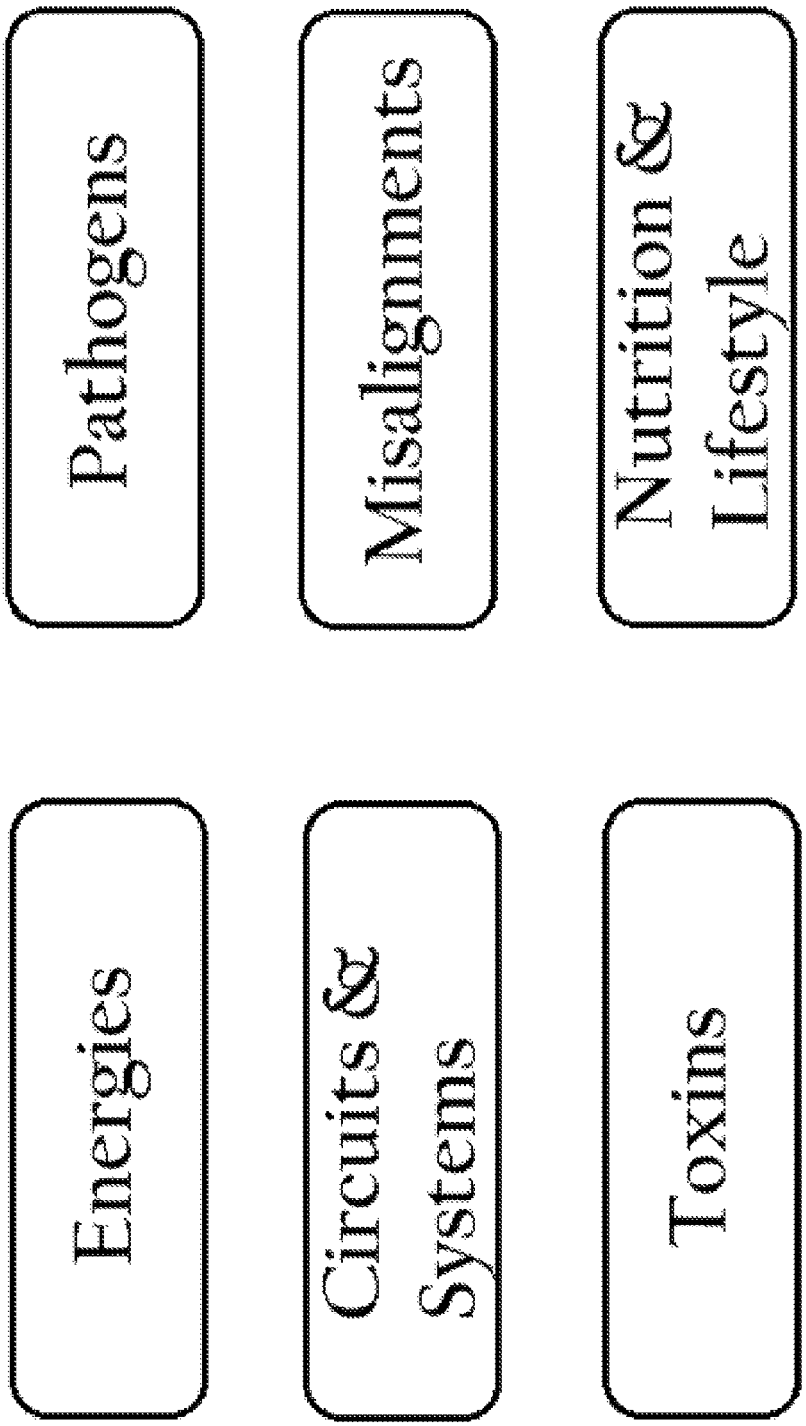
FIG. 1 illustrates an example embodiment of the general categories of a mind map
Figure 2:
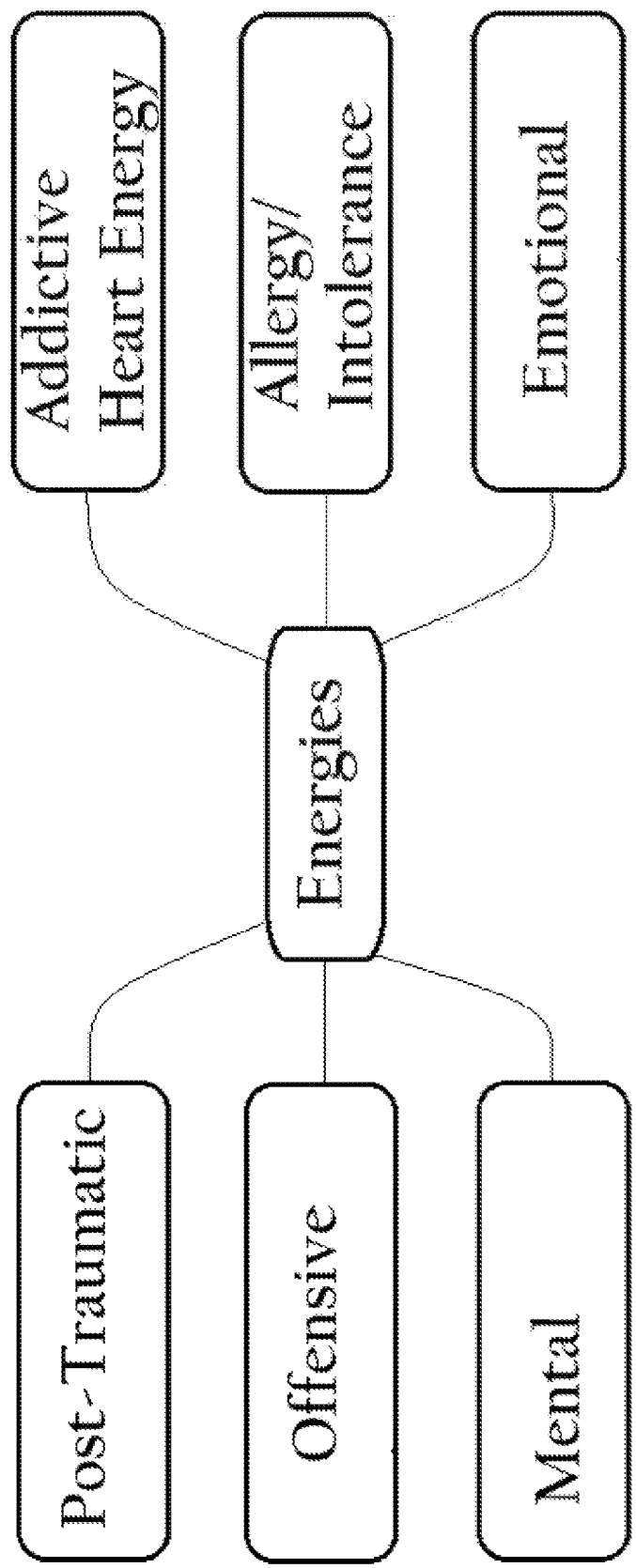
FIG. 2 illustrates an example embodiment of a subcategory of a mind map

An example configuration of the mind map, while not limiting, illustrating the six (6) categories is shown at FIG. 1. Further, each category has a unique series of subcategories and/or questions (see FIG. 2) that guide the tester in an effort to effectuate a proper identification. For example, the tester asks the subject a question based on the general categories (see FIG. 1) of the mind map and performs muscle response testing.(see FIGS. 4 and 5). The subconscious mind of a person knows, and is able to identify (through muscle testing), the category within which the body has an imbalance. Based on the response, if the subconscious mind identifies the "Energies" category from FIG. 1, the tester and/or subject are then presented with a series of subcategories illustrated generally at FIG. 2. It will be appreciated that varying arrangements, graphics, and nomenclatures may be used while not departing from the present invention. The tester then repeats the above steps (i.e., asking the subject relevant questions about the mind map) until an identification is available.

Figure 3:
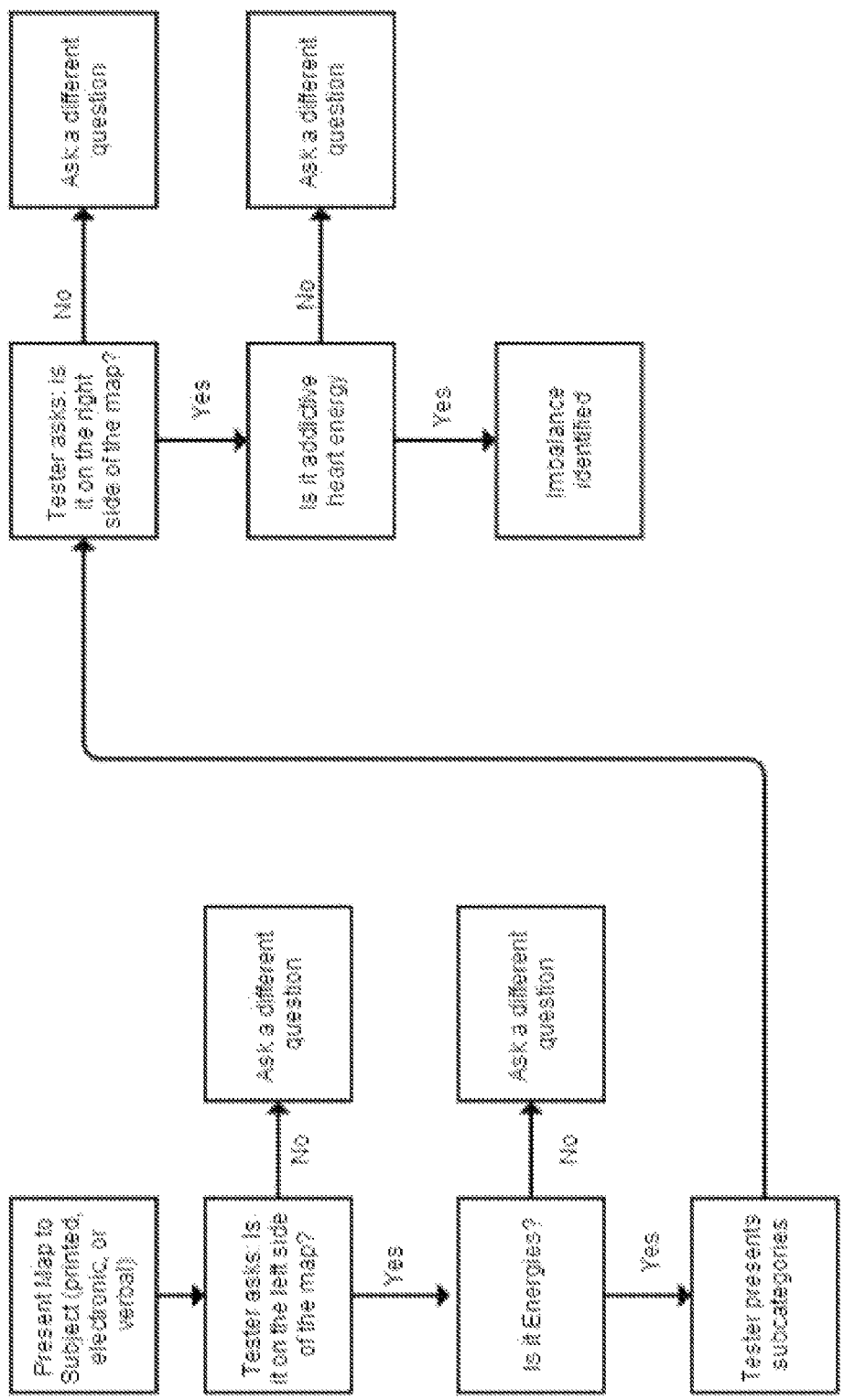
FIG. 3 illustrates an example flowchart illustrating how a user interacts with a mind map to identify an imbalance

In one embodiment, the mind map comprises a book or binder with a series of tabs directing a user from one section and/or to another, and then further within each section, until an identification is reached. For example, a tester may have a binder with a first section that has a series of beginning questions or that simply illustrates the broad categories of the mind map (see FIG. 1). The tester may then ask the outlined questions, or may simply show the subject the mind map and ask questions based on the layout of the mind map (e.g., is the ailment you are experiencing related to the left side of the mind map?). Based on the responses, the tester selects a general category and turns to the corresponding tabbed (or otherwise noted) section of the binder. Once within the sub-category (see FIG. 2), the tester then commences a series of questions to further refine and lead to other subcategories, where he/she again follows the corresponding tabs to ascertain the next series of questions. The tester continues this process until an identification is made. FIG. 3 illustrates an embodiment of the process of using the mind map to identify a bodily imbalance.

In another embodiment, a mind map is presented using an electronic means for interacting with a series of links until a final identification is made. In one embodiment the electronic means comprises a computer readable medium, such as a compact disc, ROM memory, or flash memory, that is inserted or otherwise installed onto a personal computer or other computing device. For example, a physician with a computer in the examination room may insert a compact disc into the computer and either view the files electronically, or may run an executable file that allows for installation on the computer, or that otherwise allows a user to interact with the mind map. The tester will then click on files, folders, or links to interact with the mind map and reach an identification. For example, a user will be shown the broad categories as illustrated in FIG. 1. A user will then select a category, such as by clicking, double-clicking, or the equivalent, to reach the subcategories and/or questions, e.g., FIG. 2. The user may continue to follow the links until an identification is reached.

In another embodiment, the electronic means comprises hosting the media on a $3^{rd}$ party location, such as a server, wherein a user may connect to the server using a capable device (e.g., a personal computer directly connected to the server, over the internet, or use of virtual servers) and interact with the links.

In yet another embodiment, the electronic means comprises hosting a website wherein a user may access the mind map links from any internet-capable device, such as a personal computer, tablet, smartphone, or other device; the website hosting being accomplished according to the standards and methods known to those in the art. In this manner, a tester may perform tests while away from an office setting. In other words, a tester (which may include physicians or laymen) would be able to perform the tests regardless of location. For example, a person on vacation may suffer from an illness and desire to identify the bodily imbalance. Using their phone or other internet connected device, they are able to access the website and interact with a mind map (graphical or text), thus helping them to reach an identification.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention as defined in the appended claims. In the claims, any means-plus-function clauses are intended to cover the structures described herein as performing the recited function and not only structural equivalents, but also equivalent structures. Unless the exact language "means for" (performing a particular function or step) is recited in the claims, a construction under §112(f) (formerly known as §112, 6th paragraph) is not intended. Additionally, it is not intended that the scope of patent protection afforded the present invention be defined by reading into any claim a limitation found herein that does not explicitly appear in the claim itself.

What is claimed is:

1. A method of identifying bodily imbalances using a mind map, the method comprising:
   presenting a mind map to a subject, wherein the mind map comprises one or more categories of health and wellness and one or more bodily imbalances;
   asking the subject one or more questions based on the mind map;
   performing muscle response testing on the subject after each question has been asked; and
   based upon the subject's muscle response, identifying the corresponding bodily imbalance.

2. The method of claim 1, wherein the mind map is presented in printed form.

3. The method of claim 1, wherein the mind map is presented using an electronic means.

4. The method of claim 1, wherein the mind map is presented verbally.

5. The mind map of claim 1 comprising at least six categories for identification.

6. The categories of claim 5 comprising pathogenic imbalances, structural imbalances, nutritional imbalances, circuitry imbalances, toxic imbalances, and energetic imbalances.

7. The printed form of claim 2, comprising tabbed, or otherwise noted, pages in one or more books and/or binders.

8. The electronic means of claim 3, comprising a computing device, personal computers, tablets, smartphones, or PDAs.

9. A method of identifying bodily imbalances using a mind map, the method comprising:
   presenting an interactive mind map to a subject via a computing device, wherein the mind map comprises one or more categories of health and wellness and one or more bodily imbalances;
   asking the subject one or more questions based on the mind map;
   performing muscle response testing on the subject after each question has been asked;
   interacting with the mind map on the computing device based upon the subject's muscle response; and
   identifying the corresponding bodily imbalance.

10. The interactive mind map of claim 9 comprising at least one link from a general category to a series of subcategories.

11. The at least one link of claim 10 comprising a shortcut to a local file/folder or a hyperlink to an online webpage, graphic, or chart.

12. The method of claim 9, wherein the computing device comprises a personal computer, tablet, smartphone, or PDA.

13. The method of claim 9, wherein the one or more questions elicit a "yes" or "no" response from the subject.

14. The method of claim 9, wherein interacting with the mind map comprises selecting, highlighting, clicking, or otherwise activating the underlying link to the subcategory.

15. The at least one category of claim 10 comprising pathogenic imbalances, structural imbalances, nutritional imbalances, circuitry imbalances, toxic imbalances, and/or energetic imbalances.

16. A method of identifying bodily imbalances using a mind map, the method comprising:
   presenting an interactive mind map to a subject via a computing device, wherein the mind map comprises one or more illustrated categories of health and wellness and one or more bodily imbalances;
   asking the subject a series of questions based on the one or more categories in the mind map;
   performing muscle response testing on the subject for each respective question;
   based on the subject's muscle response to each question, clicking a corresponding hyperlink to reach a subcategory; and
   continuing to ask questions and perform muscle testing in combination with the presented categories and imbalances until a final bodily imbalance is identified.

* * * * *